United States Patent [19]

Edwards et al.

[11] Patent Number: 4,824,819

[45] Date of Patent: Apr. 25, 1989

[54] VANADIUM COATED PHOSPHORUS-VANDIUM OXIDE AND PHOSPHORUS-VANADIUM OXIDE CO-METAL CATALYST AND PROCESS FOR THE MANUFACTURE OF MALEIC ANHYDRIDE

[75] Inventors: Robert C. Edwards; William S. Eryman, both of Naperville, Ill.

[73] Assignee: Amoco Corporation, Chicago, Ill.

[21] Appl. No.: 154,788

[22] Filed: Feb. 10, 1988

[51] Int. Cl.$^4$ .................... B01J 27/198; B01J 27/18; C07D 307/34
[52] U.S. Cl. ................................. 502/209; 502/211; 549/259
[58] Field of Search ........................................ 502/209

[56] References Cited

U.S. PATENT DOCUMENTS

| | | | |
|---|---|---|---|
| 3,888,886 | 6/1975 | Young et al. | 502/209 |
| 4,151,116 | 4/1979 | McDermott | 502/209 |
| 4,416,803 | 11/1983 | Udovich et al. | 502/209 |
| 4,418,003 | 11/1983 | Udovich et al. | 502/209 |
| 4,515,904 | 5/1985 | Edwards | 502/209 |
| 4,560,674 | 12/1985 | Wrobleski et al. | 502/209 |
| 4,563,439 | 1/1986 | Bremer et al. | 502/209 |

*Primary Examiner*—Paul E. Konopka
*Attorney, Agent, or Firm*—Gunar J. Blumberg; William H. Magidson; Ralph C. Medhurst

[57] ABSTRACT

A catalyst for the oxidation of butane to produce maleic anhydride comprising a substrate containing phosphorus and vanadium or alternatively phosphorus, vanadium and a co-metal characterized by the presence of post deposited vanadium. A process for the manufacture of maleic anhydride from butane feedstock using the novel catalyst is also described. Maleic anhydride is useful in the manufacture of alkyd resins.

21 Claims, No Drawings

VANADIUM COATED PHOSPHORUS-VANDIUM OXIDE AND PHOSPHORUS-VANADIUM OXIDE CO-METAL CATALYST AND PROCESS FOR THE MANUFACTURE OF MALEIC ANHYDRIDE

This invention relates to the preparation of maleic anhydride by the catalytic molecular oxidation of butane and is more particularly concerned with an improved catalyst for use in carrying out that oxidation.

Maleic anhydride is of significant commercial interest throughout the world, and is extensively used in the manufacture of alkyd resins. It is also a versatile intermediate for chemical syntheses. Consequently, large quantities of maleic anhydride are produced each year to satisfy these needs.

In general, catalysts proposed for the oxidation of butane to maleic anhydride have been based upon vanadium and phosphorus. Thus, the use of a vanadium-phosphorus complex catalyst to oxidize butane to maleic anhydride is described in Bergman et al., U.S. Pat. No. 3,293,268. This catalyst, however, requires an operating temperature greater than 500° C. and, in general, reported yields are relatively low and not commercially attractive. In order to improve the effectiveness of vanadium-phosphorus catalysts, it has been proposed to incorporate various additives, frequently referred to as "activators", "stabilizers", "promoters", and the like. For example, Freerks et al., U.S. Pat. No. 3,832,359, proposes the addition of iron to phosphorus and vanadium, and Raffelson, U.S. Pat. No. 3,867,411, further modifies the iron-modified phosphorus vanadium catalyst by the addition of chromium. Boghosian, U.S. Pat. No. 3,862,246, adds to phosphorus and vanadium a catalyst activator which is zinc, bismuth, copper or lithium. In British Pat. No. 1,475,309, it is proposed to increase the effectiveness of a phosphorus-vanadium catalyst by adding an activator which is cobalt or nickel. British Pat. No. 1,460,971 is concerned with a catalyst in which the added component is titanium, zirconium, hafnium or silicon. Young et al., U.S. Pat. No. 3,888,886, discloses phosphorus-vanadium catalysts modified with various transition metals having varying effectiveness, the more active being chromium, iron, hafnium, zirconium, cerium and lanthanum. Although other metals are disclosed, they are characterized as having little or no activity.

While these various additives do bring about some improvement in the phosphorus-vanadium catalyst suitable for oxidizing butane to maleic anhydride, there remains much room for improvement, particularly from the standpoint of high conversions and yields.

It is accordingly an object of this invention to provide an improved catalyst based upon phosphorus and vanadium.

It is a further object of the invention to provide a catalyst of the character indicated which is of particular effectiveness in the oxidation of butane to maleic anhydride.

An object of the present invention is to provide a phosphorus-vanadium catalyst impregnated with vanadium. A further object of the present invention is to provide a process for the manufacture of a phosphorus-vanadium-co-metal catalyst impregnated with vanadium. An additional object is to provide a process for the manufacture of maleic anhydride in the presence of the novel catalyst. Suitable co-metals include zinc, molybdenum, tungsten, uranium, titanium, tin, cobalt, chromium, manganese, iron, nickel, copper, bismuth, antimony or mixtures thereof, and the preferred co-metals are zinc and molybdenum.

These and other objectives are realized in accordance with the present invention by a catalyst comprising a substrate containing phosphorus and vanadium, and optionally containing a promoting or activating additive, and a promoter deposited upon the substrate after the substrate has been formed, i.e., a "post-deposited" promoter. More particularly, the catalyst of this invention comprises a pre-formed substrate containing phosphorus and vanadium, and post-deposited vanadium.

The term "substrate" is used to designate a catalyst composition which has been prepared in any convenient manner, e.g., by any of the processes well-known to the art, and has been dried and can, in itself, serve as a catalyst in the oxidation of butane to produce maleic anhydride. This preformed catalytically active substrate is, however, in accordance with the invention, treated so that it is significantly more effective as a catalyst by having vanadium applied to its surface.

Best results are obtained in accordance with the invention when the phosphorus and vanadium are present in the substrate in the atomic ratio of about 0.8:1 to about 2:1, preferably about 1:1 to about 1.7:1, although other ratios may be employed. Generally, the ratio of phosphorus to vanadium is at least about 1.2:1 to about 1.6:1, and not more than about 1.7:1. The amount of the integrally incorporated activator in the substrate, expressed as an atomic ratio in relation to V, is variable over a wide range, but generally it lies in the range of about 0.001 to about 0.5 atom per atom of vanadium in the substrate. Preferably, however, the amount of activator is about 0.005 to about 0.3 atom per atom of vanadium, and most preferably about 0.01 to about 0.2 atom per V atom.

Similarly, the amount of post-deposited vanadium may vary over a large range, but preferably it is at least 0.001 atom per atom of vanadium in the substrate. Typically, the amount of the post-deposited vanadium will lie within the range of about 0.003 to about 0.8 atom per atom of vanadium, and preferably the amount will be in the range of about 0.02 to about 0.5 atoms per vanadium atom.

When the atomic amount of phosphorus in the substrate is taken as 1, the amount of integrally incorporated activator will typically be about 0.001:1 to about 1:1, preferably about 0.004:1 to about 0.6:1, and most preferably about 0.008:1 to about 0.4:1, whereas the amount of post-deposited promoter will typically be about 0.003:1 to about 0.5:1, preferably about 0.02:1 to about 0.2:1.

The catalyst of this invention can be prepared in any convenient manner, e.g., using techniques already known by persons skilled in the art. The following procedures, however, have been found to be particularly suitable and to yield catalysts of favorable activity. It will be understood, however, that the invention is not limited to catalysts prepared by these particular methods of preparation. Thus, the substrate of the catalyst is preferably prepared by forming a solution of a vanadium compound, a phosphorus compound, and if used, a compound of the activator metal in an appropriate solvent, concentrated hydrochloric acid, alcohols, and ethers being particularly suitable as solvents for the substrate components.

If the substrate is to be used in non-supported form, e.g., in the form of a pellet or other shape, the solution is evaporated to dryness and the resulting finely divided particles are pelletized or formed into other shapes in conventional manner.

On the other hand, if the substrate is to be in supported form, the aqueous or organic acidic solution is deposited upon a support or carrier and dried. The drying of the solution by evaporation of its aqueous content is readily effected merely by heating it in air or in an inert atmosphere, e.g., in nitrogen at about 125° C. to about 200° C., typically about 175° C. until dried. Thereafter, the dried composition, either in supported form or as a powder, or after forming, may be activated by calcination, preferably in air, at a temperature of at least about 260° C. Preferably, the catalyst is activated before forming. Alternatively, activation can be accomplished with oxygen or in an inert atmosphere, e.g., with nitrogen, argon, or other inert gas.

The phosphorus, vanadium and co-metal are suitably incorporated in any convenient form, depending upon the particular solvent being used to place them in solution, as will be well understood by persons skilled in the art. Suitable co-metals include zinc, bismuth, copper, molybdenum, tungsten, uranium, titanium, tin, cobalt, chromium, manganese, iron, nickel, antimony or mixtures thereof. While hydrochloric acid, e.g., in concentrated form or in constant boiling form, alcohols, and ethers are the preferred solvents, [other solvents are advantageously used, depending upon the form of the compound being employed.]

Thus, suitable phosphorus compounds include phosphoric acid, such as metaphosphoric acid, orthophosphoric acid, triphosphoric acid and pyrophosphoric acid, phosphorus oxides, such as phosphorus pentoxide, phosphorus halides and oxyhalides, such as phosphorus oxychloride, phosphorus pentachloride and phosphorus oxybromide, phosphorus salts such as mono-, di- and tri-ammonium phosphates, and organophosphorus compounds such as ethyl phosphate and methyl phosphate. However, phosphoric acids, such as orthophosphoric acid, phosphorus pentoxide, and phosphorus oxyhalides are preferred.

Representative of vanadium compounds which can be employed are vanadium oxides, such as vanadium pentoxide and vanadium trioxide; vanadium halides and oxyhalides, such as vanadium trichloride, vanadium tribromide, vanadyl chloride, vanadyl trichloride, vanadyl dichloride, vanadyl bromide, vanadyl dibromide and vanadyl tribromide; vanadium-containing acids such as metavanadic acid and pyrovanadic acid, and vanadium salts, both organic and inorganic, such as ammonium metavanadate, vanadium sulfate, vanadium phosphate, vanadyl formate, vanadyl acetoacetonate and vanadyl oxalate. Vanadium pentoxide is, however, preferred.

Similarly, a wide variety of compounds can be employed to introduce the vanadium element into the substrate. These activator compounds, however, should be at least partially soluble in the solvent medium used in the particular preparation in order to be best suited for combination with the phosphorus and vanadium components of the substrate.

The vanadium to be post-deposited upon the substrate in accordance with this invention is preferably applied to the substrate in a form which does not attack the substrate. Water, for example, does tend to have an adverse action and it is preferred, therefore, to employ an organic solvent. Any organic solvent such as an ether, e.g., dibutyl ether or tetrahydrofuran, an alcohol, e.g., methanol, a ketone, e.g., methylethyl ketone, a carboxylic acid, e.g., acetic acid, a nitrogen-containing compound, e.g., formamide and ethylene diamine and the like are suitably used. The invention is thus in no way limited to the use of any particular solvent but tetrahydrofuran and methanol are preferred. The vanadium should, therefore, be in a form which is at least partially soluble in the solvent to be used. Typically, the vanadium will be in the form of a salt, e.g., an inorganic salt such as a chloride, bromide or iodide, or an organic salt such as a formate or acetate.

As previously mentioned, the substrate is formed by combining the phosphorus component, the vanadium component and, if used, the co-metal component in a solution and then evaporating the solution to dryness to form a dry particulate mass or, if the substrate is to be supported, the solution is applied to the support or carrier particles and thereafter evaporated to dryness to provide support or carrier particles coated or impregnated with the catalytic components of the substrate. Although it is not essential from the standpoint of the invention, it is desirable that a substantial portion, e.g., at least about 50%, of the vanadium be in the tetravalent form.

Following the drying of the solution containing the substrate components, the dried particulate mass is preferably formed into a shape suitable for use in a butane oxidation reactor, e.g., the particles can be pelletized or prilled or tabletted or otherwise formed into structures. As previously mentioned, the particles are preferably activated, as described below, before they are shaped. Methods for shaping catalyst particles are well-known to the art and form no part of the present invention.

The dried substrate, whether in its initial particulate form which may be first subdivided, e.g., for use in a fluid-bed reactor or in its shaped form, e.g., as pellets, or in supported form, is then "activated" in the manner previously mentioned by heating it at an elevated temperature, e.g., at least about 250° C. in the presence of oxygen suitably in the form of air on in an inert atmosphere, preferably for a period of 30 to 600 minutes. If the activation is effected in an air or oxygen atmosphere, care should be taken to keep the temperature below 500° C. in order to avoid undue oxidation of tetravalent vanadium to pentavalent vanadium in order that an appreciable portion of the vanadium in the activated substrate will be present in the tetravalent form.

In accordance with the invention, the substrate is coated or impregnated with the vanadium. The procedure for applying the vanadium to the substrate is in no way critical and procedures such as used in coating a carrier may be used. Typically, the vanadium solution may be used in a volume equal to the void space of the substrate and, when added to the substrate, the solution may be imbibed by the substrate pores. Alternatively, the substrate may be immersed in an excess volume of vanadium solution, then removed and allowed to drain. The concentration of vanadium in the solution is selected so that the desired quantity of vanadium is retained by the catalyst. In a third method, the vanadium solution is sprayed upon the particles or shapes of substrate, which are tumbled to achieve uniformity. The thus-treated substrate is then dried and activated in the manner described above in connection with making a supported substrate. If desired, activation can be effected in the reactor in which the catalyst composition of the invention is to be employed, i.e., by so-called in situ activation. In this case, the catalyst is charged to the reactor and a butane-air mixture is passed through it at temperatures of 350° to 450° C. for 2 to 12 hours.

This disclosure pertains to the novel preparation of a heterogeneous catalyst for oxidizing hydrocarbons in the vapor phase with air to produce high yields of maleic anhydride. Phosphorus-vanadium and phosphorus-vanadium-co-metal catalysts prepared by various methods are impregnated with vanadium compounds. These new catalysts are substantially improved over catalysts which are not impregnated with vanadium in their ability to afford high yields of maleic anhydride from n-butane. The advantages of this type of catalyst are improved yields of maleic anhydride, low cost preparation, and long catalyst life.

Phosphorus-vanadium and phosphorus-vanadium-co-metal hydrocarbon oxidation catalysts can be prepared by a variety of methods. In a suitable process vanadium pentoxide is dissolved and reduced in aqueous hydrochloric acid. If desired, a co-metal such as molybdenum or zinc can be present at this time. When the vanadium pentoxide is completely dissolved, and a substantial reduction of vanadium (V) to vanadium (IV) has occurred as indicated by the blue color of the solution, 85% orthophosphoric acid is added to form a solution of the phosphorus-vanadium or phosphorus-vanadium-co-metal catalyst.

Most of the water-hydrogen chloride is distilled from the solution leaving a thick, blue catalyst syrup which can then be dried to give a solid catalyst precursor. However, it is preferred that this syrup be treated with organic solvents such as methanol to improve the surface area and porosity of the catalyst. This method is described in U.S. Pat. No. 4,416,802, which patent is incorporated herein by reference. To further improve this type of catalyst, aromatic acids or anhydrides are advantageously added to the methanolic solution of the catalyst syrup.

Another process for preparing a catalyst substrate is reported in U.S. Pat. No. 4,418,003, incorporated herein by reference. Vanadium pentoxide is dissolved and substantially reduced in methanol using HCl gas. A co-metal such as zinc or molybdenum can also be present. $P_2O_5$ dissolved in methanol is added to make a soluble vanadium-phosphorus or vanadium-phosphorus-co-metal catalyst. The solvent is removed to give a thick syrup which is dried to form a solid catalyst precursor.

The preferred method for preparing the catalyst substrate is disclosed in U.S. Pat. No. 4,515,904, incorporated herein by reference. Vanadium pentoxide, a co-metal such as zinc or molybdenum, and a small amount of water are put into an ether solvent such as the preferred solvent tetrahydrofuran. Phosphoryl chloride, $POCl_3$, is added slowly to the slurry. The water reacts with the $POCl_3$ to generate anhydrous phosphoric acid and hydrogen chloride gas.

$$POCl_3 + 3H_2O \rightarrow H_3PO_4 + 3HCl$$

The hydrogen chloride dissolves the $V_2O_5$ and cometal or cometal compound and reduces the $V^{+5}$ to $V^{+4}$ upon reflux.

$$V_2O_5 + 6HCl \longrightarrow 2VOCl_3 + 3H_2O$$

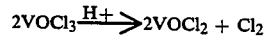

$$2VOCl_3 \xrightarrow{H+} 2VOCl_2 + Cl_2$$

While the reaction solution is being refluxed, a modifier such as o-xylene or phthalic anhydride can be added to the solution. O-xylene is the preferred modifier.

After an extended reflux of 1 to 24 hours, the solvent is removed by distillation until a thick syrup is formed. The syrup is dried overnight in a vacuum oven under an air purge at 120° to 150° C. with 0 to 15 in. Hg vacuum.

After the solid catalyst precursors are obtained, they are suitably impregnated with solutions of vanadium compounds and then fluid bed calcined in air. The calcined vanadium-impregnated powder is then formed into spheres or cylinders using graphite, Sterotex, or other lubricants. The catalyst precursors are suitably calcined prior to impregnation or formed into shapes before impregnation. The vanadium compounds used for impregnating the powder, calcined powder, or tabletted powder, can vary depending on the solvent used. Vanadyl acetylacetonate, $VOCl_2$, $VOCl_3$, $VCl_4$, and $VOSO_4$ are examples of vanadium compounds which are used advantageously for impregnating the catalyst substrate. A solution of $VOCl_3$ in tetrahydrofuran is the preferred vanadium solution for impregnating the catalyst substrate. Loadings of vanadium on the substrate catalyst may vary from 0.1 to 10 wt. % based on the weight of the substrate catalyst. Loadings of 1 to 5 wt. % are preferred.

These catalysts can be activated in air and butane or in air and butane with small amounts of triethylphosphate and water added to the feedstream. Other phosphorus compounds such as phosphites or alkylphosphates can also be used.

Butane is oxidized in the presence of the above-described catalyst of this invention in any conventional manner, and the catalyst is useful in both fluid-bed reactors, and in fixed-tube reactors and the conditions of operation of such reactors are well-known to persons skilled in the art. Typically, the oxidation of butane to maleic anhydride is carried out by means of air or other molecular oxygen-containing gases such as mixtures of carbon dioxide and oxygen or mixtures of nitrogen or steam with air or oxygen. Air is preferred. The oxidation is carried out at temperatures of 350° to 500° C., preferably 380° to 450° C. Preferably the concentration of butane in the feed will be 0.8 to 1.6 volume % with $O_2$ above 10 volume % and space velocities of 1000 to 4000 hr. are preferably employed in fixed bed reactions and 500 to 2000 hr. in fluidized bed operations. The reaction may be carried out at atmospheric, sub-atmospheric or super-atmospheric pressure, but substantially atmospheric pressure is preferred. Typically, the reaction pressure is about 1 to 7 atmospheres absolute. As previously mentioned, the reaction can be carried out in any reactor suitable for effecting vapor-phase oxidation reactions, but preferably the fixed catalyst bed is employed. The catalyst-containing tubes of such reactors can vary in diameter from, for example, 0.25 inch to 1.5 inches and the length can vary from, for example, 6 inches to 10 feet or more. It is desirable to have the surfaces of the reactors at relatively constant temperature, and some medium to conduct heat from the reactors is desirable to aid temperature control. Such media include Woods metal, molten sulfur, mercury, molten lead and eutectic salt baths. A metal block reactor whereby the metals surrounding the tube act as a temperature-regulating body is also initially used. The reactor or reaction tubes are suitably formed from any convenient material, typically stainless steel or carbon steel.

Maleic anhydride prepared by using the catalyst of this invention can be recovered by any number of means well-known to those skilled in the art. For example, the maleic anhydride can be recovered by direct condensation, or by absorption in suitable media, e.g., water with subsequent separation, dehydration and purification.

The following examples will serve to provide a fuller understanding of the invention, but it is to be understood that these examples are given for illustrative purposes only, and are not to be interpreted as limiting the invention in any way. In the examples, the terms "conversion," "selectivity," and "yield" have their conventional meanings in this art, viz.

$$\text{Conversion \%} = \frac{\text{moles n-butane reacted}}{\text{moles n-butane fed}} \times 100$$

$$\text{Selectivity \%} = \frac{\text{moles maleic anhydride produced}}{\text{moles n-butane reacted}} \times 100$$

$$\text{Yield wt \%} = \frac{\text{grams maleic anhydride produced}}{\text{grams butane fed}} \times 100$$

EXAMPLE 1

A 12 l, 3-neck, round-bottom flask equipped with a mechanical stirrer, reflux condenser, thermocouple and an electrical mantle was charged with 364 g of $V_2O_5$, 6 l of 38% hydrochloric acid, and 17.6 g of $MoO_3$. The red-brown slurry was refluxed for 4.5 hours causing the $V_2O_5$ and $MoO_3$ to dissolve and the color to turn dark blue. At this time 592 g of 85% orthophosphoric acid were added to the solution. About 5 l of water and hydrogen chloride were removed by distillation until the temperature of the syrup reached 134° C. A portion of this syrup, 210 g, was blended with 10 g of phthalic anhydride. This syrup was dried overnight in a vacuum oven at 10 in. of Hg vacuum and 120° to 130° C. with an air purge passing through the oven.

The dried catalyst precursor was crushed, mixed with 5% graphite, and formed into 3/16" cylindrical tablets having a 6 to 7 lb side crush strength. A 6 cm³ volume of this catalyst, 6.1 g, was charged to a 0.62" internal diameter minireactor and evaluated with a feed of 1.1% n-butane in synthetic air at 1200 VHSV. After 41 days onstream, this catalyst gave a maximum maleic anhydride yield of 80 wt. % at 833° F. and 75% conversion.

EXAMPLE 2

Fresh catalyst pellets from Example 1 were treated with a methanolic solution of vanadyl acetylacetonate by immersing them for four seconds in 100 ml of methanol containing 0.4 g of vanadyl acetylacetonate. The treated pellets were dried in an oven overnight at 140° C. and 10 in. of Hg vacuum with a slight air purge passing through the oven.

A 6 cm³ volume of this catalyst, 6.13 g, was evaluated as in Example 1. This catalyst gave an 89 wt. % yield of maleic anhydride at 828° F. and 82% conversion after 22 days on-stream. The improved performance of this vanadium-treated catalyst compared to the catalyst in Example 1 illustrates the benefits of vanadium impregnation—faster activation and higher yields.

EXAMPLE 3

A 3 l, 3-neck, round-bottom flask equipped with a mechanical stirrer, reflux condenser, thermocouple, and an electrical mantle was charged with 1.5 l of 38% hydrochloric acid, 9 g of $V_2O_5$, and 4.4 g of $MoO_3$. The red-brown slurry was refluxed for three hours causing the $V_2O_5$ and $MoO_3$ to dissolve and the color to turn dark blue. The blue solution was refluxed for one additional hour after 172.5 g of 85% orthophosphoric acid were added. About 1200 ml of water and hydrogen chloride were removed until the temperature of the syrup in the flask reached 130° C. O-xylene, 150 ml, 400 ml of methanol, and 15 g of phthalic anhydride were added to the blue syrup upon cooling. The solution was refluxed for 18 hours. Solvent was removed by distillation until the temperature of the syrup reached 105° C. The syrup was dried in a vacuum oven at 120° to 130° C. and 5 in. of Hg vacuum with a small air purge passing through the oven.

The catalyst precursor was crushed, mixed with 5% graphite, and formed into 3/16" cylinders having a 5.5 to 6.5 lb side-crush strength. A 6 cm³ volume of this catalyst, 6.77 g, was evaluated in a minireactor as disclosed in Example 1. After 22 days, this catalyst having a P/V/Mo atomic ratio of 1.5/1/0.03 gave a maximum maleic anhydride yield of 80 wt. % at 831° F. and 72% conversion.

EXAMPLE 4

Catalyst precursor powder from Example 3, 50 g, was added to a solution of 0.5 g of vanadyl acetylacetonate in 100 ml of methanol. The solvent was evaporated slowly while stirring the slurry. When the slurry became a thick paste, it was dried in a vacuum oven at 140° to 150° C. and 5 in. of Hg vacuum with a slight air purge. The dried powder was mixed with 5% graphite and formed into 3/16" cylinders having a 7 to 7.5 lb side-crush strength. A 6 cm³ volume of this catalyst, 5.99 g, was evaluated as in Example 1. After 27 days on-stream, the catalyst impregnated with 0.2 wt. % vanadium gave an 85 wt. % yield of maleic anhydride at 826° F. and 82% conversion. This example demonstrates that a substrate catalyst having a P/V atomic ratio of 1.5/1 can be improved with vanadium impregnation.

EXAMPLE 5

The catalyst precursor powder from Example 3 was impregnated as in Example 4, except that 40 g of powder were added to a solution of 1 g of vanadyl acetylacetonate in 50 ml of methanol. The 3/16" cylinders formed from this dried powder has a 6.5 to 7.5 lb side-crush strength.

A 6 cm³ volume of this catalyst, 5.97 g, was evaluated as described in Example 1. After 29 days on-stream, this catalyst gave a 92 wt. % yield of maleic anhydride at 833° F. and 84% conversion. This example illustrates the sensitivity of the catalyst performance to the amount of vanadium impregnation. The catalyst in this example with 0.5 wt. % vanadium impregnation has a 7 wt. % better yield than the catalyst in Example 4 and 12 wt. % better yield than the catalyst in Example 3.

EXAMPLE 6

Using the same experimental set-up described in Example 3, 106.5 g of $P_2O_5$ were dissolved in 500 ml of methanol. To this solution was added 91 g of $V_2O_5$ and 4.3 g of $MoO_3$. HCl gas was added slowly until the $V_2O_5$ and $MoO_3$ dissolved and the temperature of the solution started to decrease. O-xylene, 200 ml, was then added and the solution was refluxed for 22 hours. Solvent was removed from the blue solution until a thick, blue syrup remained. The syrup was dried in an oven at 80° C. with an air purge passing through the oven to give a blue solid. The blue solid was crushed, mixed with 5% graphite, and formed into 3/16" cylindrical tablets having a 6 to 7 lb side-crush strength.

A 6 $cm^3$ volume of this catalyst, 5.56 g, was evaluated as described in Example 1. After 36 days on-stream, this catalyst gave a maleic anhydride yield of 83 wt. % at 821° F. and 82% conversion.

EXAMPLE 7

Catalyst powder from Example 6, 50 g, was slurried with a solution of 1.7 g of $VOCl_3$ in 50 ml of tetrahydrofuran. The slurry was dried in an oven at 130° to 150° C. under an air purge. The impregnated powder (1 wt. % V) was mixed with 5 wt. % graphite and formed into 3/16" cylindrical tablets having a 6 to 7 lb side-crush strength. A 6 $cm^3$ charge of this catalyst, 5.55 g, was evaluated as described in Example 1. The yield of the catalyst after 27 days on-stream was 87 wt. % at 804° F. Using a catalyst substrate prepared with a different procedure, vanadium impregnation improved the catalyst performance by 4 wt. % at a lower temperature.

EXAMPLE 8

Catalyst powder from Example 6, 50 g, was slurried with 8.5 g of $VOCl_3$ in 100 ml of tetrahydrofuran. Air was blown over the slurry until the slurry became a thick paste. The paste was dried in a vacuum oven at 130° to 150° C. and 5 in. of Hg vacuum with a slight air purge. The impregnated power (5 wt. % V) was mixed with 5 wt. % graphite and formed into 3/16" cylindrical tablets. A 6 $cm^3$ load of this catalyst was evaluated as described previously. After only 21 days on-stream, the catalyst gave a maleic anhydride yield of 88 wt. % at 790° F. and 85% conversion. A maximum yield of 99 wt. % was achieved after 52 days on-stream at 741° F. and 90% conversion. In this example, the 5 wt. % loading of vanadium improved the catalyst more than the 1 wt. % loading of Example 7.

EXAMPLE 9

The same experimental set-up described in Example 3 was used to prepare this catalyst. Tetrahydrofuran, 500 ml, 91 g of $V_2O_5$, 4.3 g of $MoO_3$, and 78.3 g $H_2O$ were combined in the reaction flask. $POCl_3$, 230.3 g, was added slowly to the slurry causing the $V_2O_5$ and $MoO_3$ to dissolve and the solution to turn red-brown. O-xylene, 150 ml was added to the solution which was then refluxed for 22 hours. Solvent was removed from the dark green solution by distillation until the syrup reached a temperature of 144° C. The syrup was dried in a vacuum oven at 140° to 150° C. and 5 in. of Hg vacuum with a slight sir purge passing through the oven.

The catalyst was ground, mixed with 5% graphite, and formed into 3/16" cylinders having a 2 to 3 lb side-crush strength. A 6 $cm^3$ volume of this catalyst, 5.48 g, was evaluated as described previously. After 31 days on-stream, the catalyst gave a maleic anhydride yield of 94 wt. % at 808° F. and 89% conversion. A maximum yield of 101 wt. % at 92% conversion and 789° F. was achieved after 49 days on-stream.

EXAMPLE 10

Catalyst precursor powder from Example 9, 50 g, was slurried with a solution of 1.7 g $VOCl_3$ in 50 ml of tetrahydrofuran. The slurry was dried in an oven under an air purge at 130° to 150° C. The impregnated powder (1 wt. % V) was mixed with 5% graphite and formed into 3/16" cylindrical pellets.

A 6 $cm^3$ charge of the catalyst, 5.68 g, was evaluated as described in previous examples. This catalyst achieved a 95 wt. % yield of maleic anhydride at 794° F. and 89% conversion after 27 days on-stream. A yield of 101 wt. % at 757° F. and 89% conversion was attained at 43 days on-stream. At 54 days on-stream the catalyst gave a maximum yield of 104 wt. % at 740° F. and 89% conversion. After 175 days on-stream, the catalyst still gave a yield of 101 wt. % at 729° F. and 91% conversion.

The vanadium-impregnated catalyst in this example clearly demonstrates superior yields, rapid activation, and long catalyst life compared to the catalyst in Example 9.

EXAMPLE 11

Catalyst powder from example 9, 50 g, was slurried with a solution of 3.4 g of $VOCl_3$ in 100 ml of tetrahydrofuran. After drying the catalyst and forming it into 3/16" cylindrical tablets with a 6 to 7 lb side-crush strength, a 6 $cm^3$ volume of the impregnated catalyst (2 wt. % V) was evaluated in a minireactor as described in previous examples. The catalyst gave a 94 wt. % yield after only 11 days on-stream at 802° F. and 89% conversion. A yield of 102 wt. % at 770° F. and 91% conversion was achieved after 32 days on-stream. The catalyst gave a maximum maleic anhydride yield of 106 wt. % after 67 days on-stream at 734° F. and 93% conversion.

We claim:

1. A catalyst effective for the oxidation of butane to maleic anhydride, which catalyst comprises a solid substrate comprising phosporus and vanadium, in an atomic ratio of about 0.8:1 to about 2:1, said substrate having vanadium post-deposited upon its surface, said catalyst being prepared by treating said substrate, after said substrate is formed, with a vanadium compound to deposit upon said substrate at least 0.001 atom of post-deposited vanadium per atom of vanadium in the substrate.

2. The catalyst of claim 1, wherein said vanadium compound is a member of the group consisting of vanadyl acetylacetonate, $VOCl_2$, $VOCl_3$, $VCl_4$, and $VOSO_4$.

3. The catalyst of claim 1, wherein said catalyst is prepared by treating said substrate with a vanadium compound to deposit upon said substrate an amount of vanadium that falls in the range of about 0.003 to about 0.8 atom of post-deposited vanadium per atom of vanadium in the substrate.

4. The catalyst of claim 1, wherein said treating of said substrate comprises impregnating said substrate with one or more vanadium compounds.

5. The catalyst of claim 2, wherein said catalyst is prepared by impregnating said substrate with a solution of $VOCl_3$ in tetrahydrofuran.

6. The catalyst of claim 3, wherein said catalyst is prepared by treating said substrate with said vanadium compound to deposit vanadium on said substrate in an amount in the range of about 0.1 wt % to about 10 wt %, based on the weight of the substrate.

7. The catalyst of claim 6, wherein said catalyst is prepared by impregnating said substrate with a solution of $VOCl_3$ in tetrahydrofuran.

8. A catalyst effective for the oxidation of butane to maleic anhydride, which catalyst comprises a solid substrate comprising phosporus, vanadium, in an atomic ration of about 0.8:1 to about 2:1 and a co-metal selected from the group consisting of zinc, bismuth, copper, molybdenum, tungsten uranium, titanium, tin, cobalt, chromium, manganese, iron, nickel, antimony, and mixtures thereof, said substrate having vanadium post-deposited upon its surface, said catalyst being prepared by treating said substrate, after said substrate is formed, with a vanadium compound to deposit upon said substrate at least 0.001 atom of post-deposited vanadium per atom of vanadium in the substrate.

9. The catalyst of claim 8, wherein said co-metal is molybdenum.

10. The catalyst of claim 8, wherein said vanadium compound is a member of the group consisting of vanadyl acetylacetonate, $VOCl_2$, $VOCl_3$, $VCl_4$, and $VOSO_4$.

11. The catalyst of claim 8, wherein said catalyst is prepared by treating said substrate with a vanadium compound to deposit upon said substrate an amount of vanadium that falls in the range of about 0.003 to about 0.8 atom of post-deposited vanadium per atom of vanadium in the substrate.

12. The catalyst of claim 8, wherein said treating of said substrate comprises impregnating said substrate with one or more vanadium compounds.

13. The catalyst of claim 8, wherein said co-metal is zinc.

14. The catalyst of claim 9, wherein said vanadium compound is a member of the group consisting of vanadyl acetylacetonate, $VOCl_2$, $VOCl_3$, $VCl_4$, and $VOSO_4$.

15. The catalyst of claim 10, wherein said catalyst is prepared by impregnating said substrate with a solution of $VOCl_3$ in tetrahydrofuran.

16. The catalyst of claim 11, wherein said catalyst is prepared by treating said substrate with said vanadium coumpound to deposit vanadium on said substrate in an amount in the range of about 0.1 wt. % to about 10 wt %, based on the weight of the substrate.

17. The catalyst of claim 14, wherein said catalyst is prepared by impregnating said substrate with a solution of $VOCl_3$ in tetrahydrofuran.

18. The catalyst of claim 16, wherein said catalyst is prepared by impregnating said substrate with a solution of $VOCl_3$ in tetrahydrofuran.

19. The catalyst of claim 16, wherein said co-metal is molybdenum.

20. The catalyst of claim 19, wherein said vanadium compound is a member of the group consisting of vanadyl acetylacetonate, $VOCl_2$, $VOCl_3$, $VCl_4$, and $VOSO_4$.

21. The catalyst of claim 20, wherein said catalyst is prepared by impregnating said substrate with a solution of $VOCl_3$ in tetrahydrofuran.

* * * * *

UNITED STATES PATENT OFFICE
CERTIFICATE OF CORRECTION

Patent No. 4,824,819          Dated   April 25, 1989

Inventor(s)  Robert C. Edwards & William S. Eryman

It is certified that error appears in the above-identified patent and that said Letters Patent is hereby corrected as shown below:

Col. 9, Line 54      "ml" should be --ml,--

Col. 10, Line 40-42  "vanadium, in an atomic ratio of about 0.8:1 to about 2:1, said substrate having vanadium post-deposited" should be --vanadium, said substrate having vanadium in an atomic ratio of about 0.8:1 to about 2:1 post-deposited--

Col. 11, Line 10     "tungsten" should be --tungsten,--

Col. 12, Line 15     "coumpound" should be --compound--

Signed and Sealed this

Twenty-sixth Day of December, 1989

Attest:

JEFFREY M. SAMUELS

Attesting Officer          Acting Commissioner of Patents and Trademarks